Figure 1:
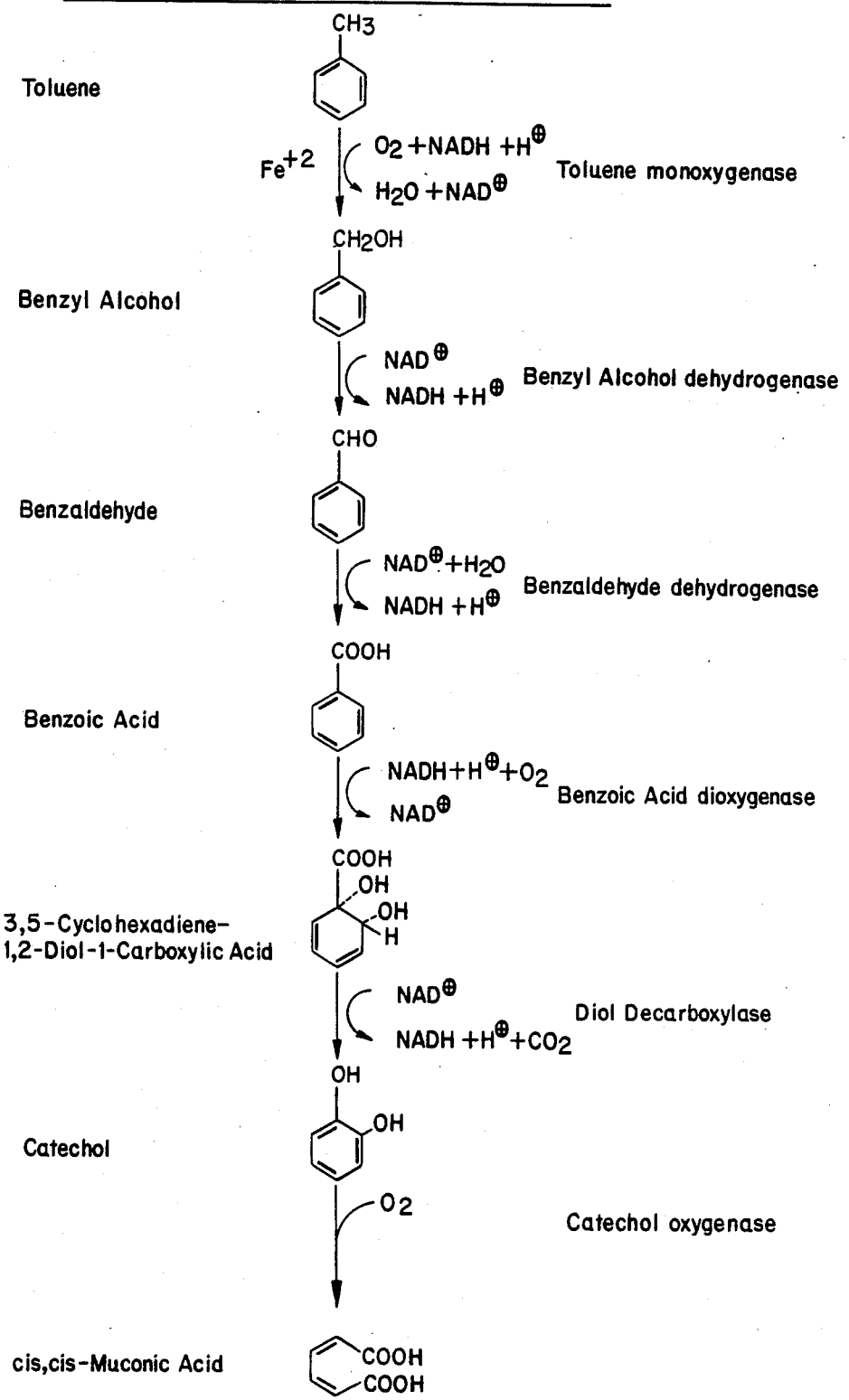

United States Patent [19]

Maxwell et al.

[11] Patent Number: 4,657,863

[45] Date of Patent: * Apr. 14, 1987

[54] STABILIZATION OF A MUTANT MICROORGANISM POPULATION

[75] Inventors: Peter C. Maxwell, New Providence; Jin-Han Hsieh, Parsippany; John C. Fieschko, Iselin, all of N.J.

[73] Assignee: Celanese Corporation, New York, N.Y.

[ * ] Notice: The portion of the term of this patent subsequent to Oct. 19, 1999 has been disclaimed.

[21] Appl. No.: 483,796

[22] Filed: Apr. 11, 1983

Related U.S. Application Data

[63] Continuation-in-part of Ser. No. 394,744, Jul. 2, 1982, abandoned.

[51] Int. Cl.[4] .............. C12N 11/00; C12N 1/20; C12P 7/40; C12P 7/44
[52] U.S. Cl. ................................ 435/142; 435/136; 435/248; 435/249; 435/253
[58] Field of Search .............. 435/136, 142, 189, 190, 435/245, 248, 249, 253, 289, 291, 815, 877

[56] References Cited

U.S. PATENT DOCUMENTS

| | | | |
|---|---|---|---|
| 2,822,319 | 2/1958 | Monod | 435/240 |
| 4,355,107 | 10/1982 | Maxwell | 435/142 |
| 4,399,220 | 8/1983 | Smiley | 435/139 |
| 4,480,034 | 10/1984 | Hsieh | 435/136 |
| 4,535,059 | 8/1985 | Hseih et al. | 435/142 |

FOREIGN PATENT DOCUMENTS

| | | | |
|---|---|---|---|
| 0071446 | 2/1983 | European Pat. Off. | 435/253 |
| 0117048 | 8/1984 | European Pat. Off. | 435/253 |

OTHER PUBLICATIONS

Froment et al, *Chem. Reactor Analysis and Design* 1979, pp. 593-594, John Wiley Publisher.

Primary Examiner—Thomas G. Wiseman
Assistant Examiner—Robin L. Teskin
Attorney, Agent, or Firm—Depaoli & O'Brien

[57] ABSTRACT

This invention provides a process for stabilizing a population of a mutant microorganism in a bioconversion system whereby growth of revertant cells is suppressed.

The process involves limiting a nutrient which is essential for cell growth so that the cells selectively grow on a growth carbon source rather than on a non-growth carbon source which is present. The revertant cells being suppressed have a similar ability as the parent strain of the mutant microorganism to grow on the non-growth carbon source in the bioconversion system.

The non-growth carbon source in the bioconversion system is metabolized to an extracellular accumulating quantity of a desired metabolite, e.g., toluene is converted to muconic acid.

4 Claims, 2 Drawing Figures

BIOCONVERSION OF TOLUENE TO MUCONIC ACID

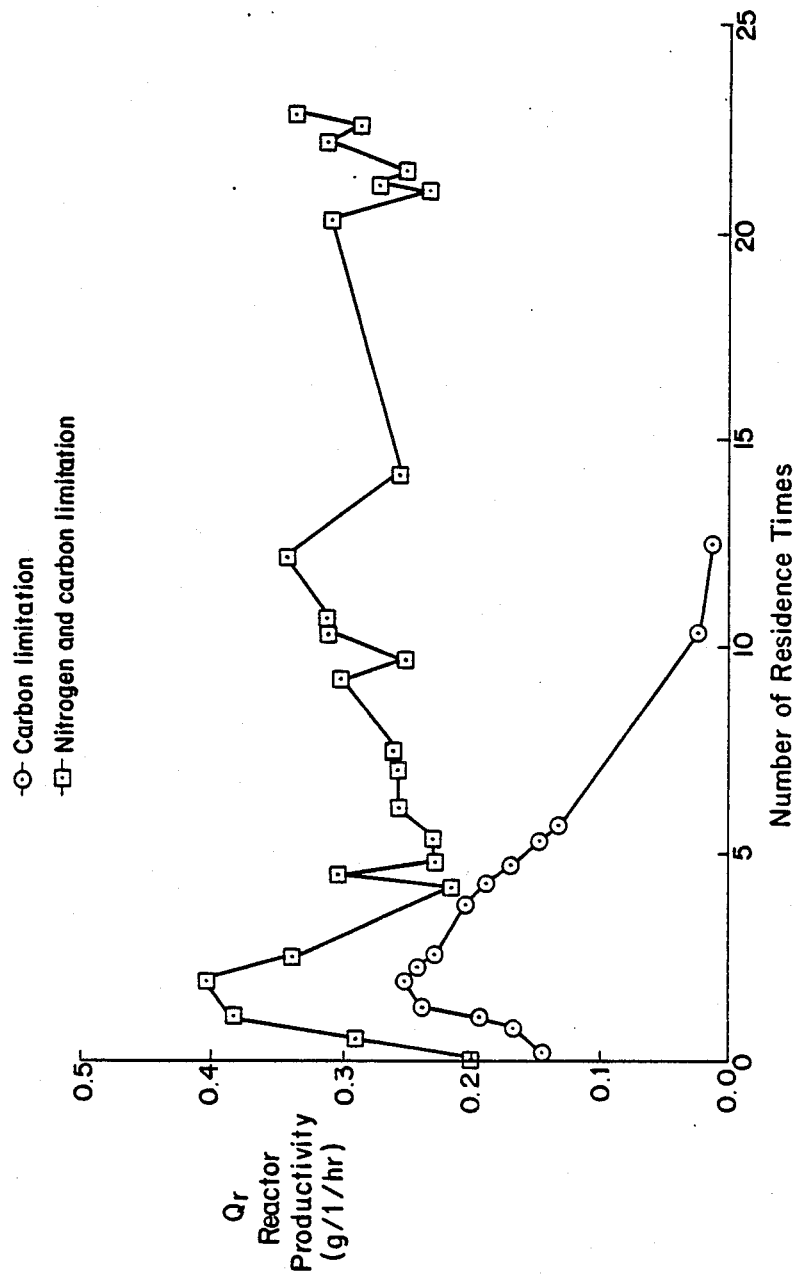

STABILIZATION OF A MUTANT MICROORGANISM POPULATION

This patent application is a continuation-in-part of patent application Ser. No. 394,744, filed July 2, 1982, now abandoned.

BACKGROUND OF THE INVENTION

Microorganisms adapt to a broad variety of environmental conditions. This versatility is characterized by the reorganization of macromolecular structure, the induction and/or suppression of enzyme systems, and the redistribution of genetic matter among cellular metabolic pools.

The theory and practice of "nutrient limitation" effects in fermentation systems is elaborated in literature such as Biochemical Engineering, Second Edition, Academic Press, New York, 1973; Biochemical Engineering Fundamentals, McGraw-Hill, New York, 1977; Principles of Microbe And Cell Cultivation, John Wiley and Sons, New York, 1975; Fermentation And Enzyme Technology, John Wiley and Sons, New York, 1979; and the like.

Biotechnology and Bioengineering, 18, 180 (1976) is directed to transient response of *Enterobacter aerogenes* under a dual nutrient limitation in a chemostat. Quantitative evidence is provided that cells can be grown under dual nutrient limitation. The pattern of response is consistent with the hypothesis, for example, that phosphate-limitation restricts nucleic acid synthesis and that nitrogen-limitation restricts protein synthesis.

In a continuous fermentation (or chemostat) mode of cultivating microorganisms, growth nutrient-limitation is necessary in order to achieve a "steady state", i.e., a constant level of cell concentration in a continuous flow reactor with a defined medium concentration.

As indicated in the literature, conventional nutrient-limitation is primarily a technique to achieve steady state continuous fermentation and to study various yield and maintenance factors of cell mass with respect to various nutrients for cell growth. For the production of conventional fermentation products, such as ethanol, citric acid, lactic acid, acetic acid, and the like (primary metabolites), or antibiotics, microbial toxins, and the like (secondary metabolites) in a continuous flow reactor, nutrient-limitation can also be used to achieve steady state product formation. However, in a chemostat this type of nutrient-limitation has little or no effect on the stability of cells, i.e., the maintenance of the production and productivity level of a specific metabolite.

With a *Pseudomonas putida* type of mutant strain, the cells can grow on a preferred growth carbon and energy source (glucose, succinate or acetate) and convert a non-growth carbon source (e.g., toluene) to a product (e.g., muconic acid). The mutant strain at least initially is unable to grow on toluene as a carbon source. However, in the presence of toluene and other nutrients over a prolonged period of time (1-2 days), cells within the population "revert"; i.e., exhibit a parent strain ability to grow on toluene. Initially only one, or perhaps a few cells revert, and eventually the reverted cell(s) grow and become the dominant cell type because of the selective ability to grow on both the growth carbon and the "non-growth" carbon sources that are present.

Accordingly, it is an object of this invention to provide a method for stabilizing a population of a mutant microorganism by suppression of the selective growth of revertant cells.

It is another object of this invention to provide a method for efficient bioconversion of toluene to muconic acid in a steady state continuous mode.

Other objects and advantages of the present invention shall become apparent from the accompanying description and examples.

DESCRIPTION OF THE INVENTION

One or more objects of the present invention are accomplished by the provision of a method of stabilizing a homogeneous population of a mutant microorganism in a bioconversion system whereby the growth of revertant cells is suppressed, which comprises limiting the presence of at least one nutrient essential for cell growth in the bioconversion system which in addition to a growth carbon source contains a non-growth carbon source that is converted by a specific metabolic pathway to a metabolite other than carbon dioxide or biomass, wherein the said revertant cells have a similar ability as the parent strain of the mutant microorganism to grow on the said non-growth carbon source in the bioconversion system.

The term "nutrient" as employed herein refers to elemental nutrients essential for cell growth in an aqueous fermentation medium, such as nitrogen, phosphorus, sulfur, magnesium, iron, calcium, zinc, sodium, copper, molybdenum, manganese, and the like. "Growth carbon" is an essential element which is excluded from the term "nutrient" for purposes of the present invention, and it is understood that growth carbon is always present in the dynamic bioconversion systems of interest.

The term "non-growth carbon" refers to a carbon source which a given mutant microorganism does not metabolize for cell growth. Typical non-growth substrates for purposes of the present invention include substituted and unsubstituted aromatic compounds such as benzene, xylene, ethylbenzene, styrene, phenol, catechol, anthranilic acid, salicylic acid, naphthalene, and the like.

The term "reversion" as noted previously refers to the phenomenon in which a homogeneous mutant microorganism population regains a parent strain ability to grow on a non-growth carbon source in a bioconversion system. The reversion phenomenon appears to involve an increasing relative frequency of a variant microorganism on the basis of a selective growth advantage provided by a specific nutrient environment.

The application of a nutrient-limitation to suppress or minimize this reversion phenomenon in bioconversion systems is novel. Thus, for microbial bioconversion processes, the nutrient-limitation aspect can be applied not only to achieve steady state production of cells and product, but also to improve the functional stability of microbial populations.

For actively growing cells, the growth carbon can be limited to reduce catabolite repression and to increase the level of enzyme induction. Under nitrogen or phosphorus or other nutrient-limited conditions, the cell growth is restricted, with the result that the cells selectively grow on a preferred carbon source, such as glucose, succinate or acetate, instead of growing on an aromatic compound or other non-growth carbon source. Consequently, the stability of a reversion-susceptible mutant strain population is improved. This growth state can be found in continuous fermentation (chemostat) and in the early stage of fed-batch fermentation.

For resting or non-growing cells under nutrient-limitation, a present invention mutant strain, after proper induction to induce enzymes and in the absence of growth nutrient, converts a non-growth carbon source to an extracellular accumulating metabolite and obtains energy from the reaction for cell maintenance, and concomitantly the population of microorganisms achieves cell stability. This situation can be found in the stationary growth phase (or later period) of a fed-batch fermentation, and in the concentrated cells of a continuous fermentation with cell recycle.

The present invention method of stabilizing a population of a mutant microorganism is generally applicable to constructed strains which are capable of metabolizing non-growth carbon sources to metabolites other than carbon dioxide and/or biomass. Such strains are derived from naturally occurring organisms such as the species *Pseudomonas putida, Pseudomonas aeruginosa, Pseudomonas fluorescens;* some members of the genera Nocardia; various unclassified fungi (both molds and yeasts); and the like, excluding nitrogen-fixing species.

In the following description the invention is more particularly illustrated with reference to metabolism of hydrocarbon substrates to metabolites such as muconic acid which are recoverable as useful products.

In the Journal Of Bacteriology, 134, 756(1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through $\beta$-ketoadipate to biomass and carbon dioxide.

The enzymes functioning in the toluene metabolism by the ortho pathway included toluene mono-oxygenase, benzyl alcohol dehydrogenase, benzaldehyde dehydrogenase, benzoate oxygenase, dihydrodihydroxybenzoate dehydrogenase, catechol 1,2-oxygenase and muconate lactonizing enzyme. The subsequently formed $\beta$-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No naturally occurring microorganisms (e.g., *Pseudomonas putida*) are known that metabolize an aromatic hydrocarbon substrate such as toluene by the ortho pathway via muconic acid and $\beta$-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of toluene as a convenient source of muconic acid requires the construction of mutant strains of microorganisms which (1) metabolize toluene by means of the ortho pathway, and (2) allow the accumulation of muconic acid without further assimilation:

This type of mutant strain can be provided by a process for microorganism construction which comprises (1) culturing microorganism species selectively to provide strain A1 which metabolizes toluene by the ortho pathway via catechol to muconic acid, and which subsequently metabolizes the resultant muconic acid via $\beta$-ketoadipate to biomass and carbon dioxide; (2) continuously and selectively culturing strain A1 for rapid growth on toluene as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts toluene to muconic acid and lacks active muconate lactonizing enzyme.

Microorganisms constructed in the manner outlined above are described in copending application Ser. No. 287,343 now U.S. Pat. No. 4,355,107 (incorporated by reference). These mutants possess a novel combination of enzymes which include catechol 1,2-oxygenase enzyme with activity that is not inhibited in the presence of less than about one gram/liter of muconic acid in a bioconversion medium.

Illustrative of these mutant microorganisms are constructed strains of fluorescent Pseudomonads each of which has the following characteristics:
  (a) possesses catechol 1,2-oxygenase enzyme with activity that is not inhibited in the presence of a low level of muconic acid in a growth medium;
  (b) lacks active catechol 2,3-oxygenase enzyme;
  (c) lacks active muconate lactonizing enzyme; and
  (d) cells are rod shaped, vigorously motile and polarly flagellated.

A specific mutant microorganism of the type described above is ATCC No. 31,916 strain of *Pseudomonas putida* Biotype A. Employing one of the constructed microorganisms described above for the production of muconic acid from toluene, the rate of toluene conversion typically is about 0.8–1.2 grams of muconic acid produced per dry weight gram of cells per hour. The conversion of toluene proceeds readily at a dry weight cell concentration of 1–3 grams per liter, with a resultant muconic acid production rate of 0.4–2 grams per liter per hour. Under optimal conditions, the muconic acid accumulation limit can approach up to about 50 grams of muconic acid per liter of growth medium. The bioconversion normally is conducted at ambient temperatures up to about 31° C. In FIG. 1 there is a schematic representation of the combination of enzymatic activities functioning for co-oxidation of toluene to muconic acid via the ortho metabolic pathway. In FIG. 1 "NAD" is nicotinamide adenine dinucleotide, and "NADH" is the hydrogenated form of NAD.

As described in the Examples and as summarized in FIG. 2, continuous production of muconic acid from toluene has been demonstrated in a chemostat using a mutant strain of *Pseudomonas putida*. Under glucose-limitation the cells readily revert to a parent-type of strain (after 2–3 residence times), and metabolize toluene for growth. Under nitrogen-limitation, the stability of the mutant strain is significantly improved (to over 20 residence times). Steady state muconic acid concentration of 10 mmoles at dilution rate 0.20 hr$^{-1}$ and specific productivity of 0.20 g product/g cells/hr is achievable.

The production of muconic acid from toluene is sensitive to the level of growth carbon (catabolite repression), nutrient concentration (i.e., cell stability), muconic acid concentration (end product inhibition and repression) and toluene level and mass transfer rate to the fermentation broth (enzyme induction and growth inhibition).

It has been found that in order to achieve higher reactor productivity for muconic acid production the excess energy generated by the bioconversion needs to be removed. During a continuous fermentation with cell recycle, a minimal amount of growth carbon and other nutrients is required for maintenance, and for growth as an energy sink to remove the excess energy generated.

The following examples are further illustrative of the present invention. The components and specific ingredients are presented as being typical, and various modifications can be derived in view of the foregoing disclosure within the scope of the invention.

For cultivation, carbon sources such as glucose, succinate and, acetate are added aseptically prior to inoculation. Incubation conditions are in 250 ml shake flasks. Shaking is in a rotary shaker with temperature controlled at 28° C.

Microbial growth is typically measured by determining the turbidity of the cell suspension in a Klett-Summerson Colorimeter using the #66 red filter. One Klett unit is equivalent to $3 \times 10^6$ cells per ml or 17.5 mg wet weight per liter or 3.52 mg dry weight per liter. Muconic acid salt is measured at 257 nm with a U.V. spectrophotometer.

Cultures are stored under liquid nitrogen.

EXAMPLE

This Example illustrates the construction of a strain of microorganism which oxidizes toluene via the ortho ($\beta$-ketoadipate) pathway.

A series of mutants which metabolize toluene through the ortho pathway is constructed by first blocking the meta pathway and then isolating phenotypic revertants which have reacquired the ability to grow on benzoate. Strains possessing a meta pathway block are isolated after penicillin plus D-cycloserine enrichment for organisms which fail to grow on benzoate. Some isolates are then spotted into agar plates and incubated in the presence of toluene. Virtually all isolates revert to growth on toluene. The plates are sprayed with 10 mM catechol and approximately 25% of the revertants are found not to produce 2-hydroxymuconic semialdehyde. None of the colorless revertants are found to possess an active catechol 2,3-oxygenase following induction with toluene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycoserine procedure to enrich for cells unable to grow on toluate.

Both these techniques are used in succession followed by counter-selection for growth on toluene. A strain designated MW 1200 is first cultured on toluene. A small portion (0.05 ml) of this culture is transferred to 50 ml of benzoate medium. After growth on benzoate the cells are transferred to toluate and incubated for approximately one hour. Penicillin D-cycloserine are then added as described above and the incubation is continued for four to six hours. Cells are harvested, washed and transferred to a toluene containing medium.

After growth on toluene the cells are plated on benzoate agar and incubated for 48 hours, and a number of large colonies and a few small colonies are formed. After spraying with catechol it is found that all of the small colonies turn yellow (indicating the presence of the meta pathway) but none of the large colonies do. Large colonies are picked and cultured and it is found that following growth on toluene, these strains contain no functional 2,3-oxygenase but are fully induced for the 1,2-oxygenase. These strains metabolized toluene by the ortho pathway. One isolate, designated MW 1210, is employed in Example II.

EXAMPLE II

This Example illustrates the construction of a *Pseudomonas putida* Biotype A strain ATCC No. 31,916 type of mutant strain.

Strain MW 1210 of Example I is subjected to continuous cultivation with toluene as the sole source of carbon. Initiall a dilution rate of 0.15 hours$^{-1}$ is employed. After the culture had stabilized, the dilution rate is increased successively to 0.25 hour$^{-1}$, 0.34 hour$^{-1}$, and 0.46 hour$^{-1}$. An isolate is made from the cells which dominates the culture at this latter dilution rate. This strain is then used to construct a strain which accumulates muconic acid to greater than one gram per liter.

The above strain is cultured overnight in liquid medium on toluene as the sole source of carbon, then benzoate is added to a level of 5 mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile de-ionized water. An aliquot of these cells is transferred to fresh medium containing 0.5 mM p-hydrobenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5 mM succinate and 5.0 mM benzoate as sole sources of carbon. After 36 hours incubation, the plate shows a mixture of large and small colonies. Cells from a number of small colonies are cultured in liquid medium, induced with toluene and tested for their ability to accumulate muconic acid. Isolate strains which accumulate muconic acid are identified.

EXAMPLE III

This Example illustrates the stabilization of a population of a mutant microorganism by means of nutrient-limitation.

Microorganism

The microorganism employed is a *Pseudomonas putida* Biotype A mutant strain (ATCC 31,916) as described in Example II. The microorganism genome contains an encoded DNA segment which enables catabolism of toluene, and enzymatic blocks are present in this toluene pathway, causing accumulation of muconic acid rather than further co-oxidation to carbon dioxide and/or biomass.

Fermentation Equipment

Fermentation runs are conducted in a New Brunswick Scientific Bioflo C-30 fermentor, a chemostat with a working volume of 350 ml. For more accurate control, a Universal Electric Neptune Dyna-Pump and a Gilson Volumetric Minipuls 2 are used for air and feed pump, respectively. The dissolved oxygen concentration of the broth is monitored using a New Brunswick Scientific dissolved-oxygen electrode and recorder. The pH is monitored and controlled at 6.2 by addition of a 5N solution of NaOH employing an Ingold pH electrode and New Brunswick Scientific controller.

Toluene is suppled to the fermentor by bubbling air through liquid toluene, and the resulting toluene-saturated air is combined with a second air stream and directed to the fermentor through a sparger. Both the air and toluene-saturated air flows are controlled and monitored by a volumetric Mathieson flow meter.

Medium

The growth medium contains the following: $Na_2HPO_4.H_2O$ (7.1 g/l), $KH_2PO_4$ (13.6 g/l), $MgSO_4$ (0.12 g/l), $CaCl_2$ (0.022 g/l) and $FeSO_4.H_2O$ (0.0051 g/l). Nitrogen is incorporated into the medium as $(NH_4)_2SO_4$ at a concentration of 2.24 g/l for carbon-limited runs, and at lower concentrations for nitrogen-limited runs. The carbon source employed is glucose, the concentrations varying from 5–10 g/l. The glucose is sterilized separately to prevent caramelization, and aseptically combined with the rest of the medium. pH is adjusted to 6.2 after sterilization by addition of 5 N NaOH.

Inoculum

The culture is maintained by weekly transfers on agar slants consisting of the above medium with 20 mM sodium acetate as the carbon source. The slants are kept in a temperature controlled incubator at 30° C.

Experimental Procedure

The chemostat is filled with 300 ml of growth medium, the temperature and pH adjusted to 30° C. and 6.2 respectively, the aeration set at 0.2 1 pm (or 0.57 vvm) and the toluene-saturated air flow rate set at 18 ml/min (or 0.05 vvm). The fermentor is then inoculated with a slant washed with 5 ml of sterile distilled water. The fermentor is run batchwise for approximately 20 hours, resulting in a cell concentration of 100–200 Klett units (red filter) which is equivalent to 0.35–0.70 g dry wt/l. The feed pump is then calibrated and set, the toluene saturated air flow rate increased to 30–45 ml/min (depending on the experiment) and continuous operation commenced.

Analytical Methods

Glucose concentration is measured using an enzymatic assay based on the use of hexokinase and glucose-6-phosphate dehydrogenase (Sigma Chemical Company). Muconic acid is measured spectrophotometrically at 257 nm on a Beckman Model 25 spectrophotometer. Cell concentration is measured using a Klett-Summerson Photoelectric Colorimeter (red filter) which is correlated to g/dry cell wt/liter by a calibration curve.

Nutrient-limitation Results

FIG. 2 illustrates a typical carbon-limited fermentation, at a dilution rate of 0.179 $hr^{-1}$. The instantaneous specific productivity $Q_p$ (g muconic acid/g cell/hr), not shown in FIG. 2, and the instanteous reactor productivity $Q_r$ (g muconic acid/liter/hr) reach a maximum at approximately 2–3 residence times. Subsequently, the muconic acid concentration in the broth and consequently the values for both $Q_r$ and $Q_p$ begin to decrease. These phenomena are noted in three separate carbon-limited fermentations at three different dilution rates. These results indicate that revertant cell growth is occurring, which revertant cells metabolize and grow on toluene.

Under nitrogen-limited and essentially carbon-limited conditions, the growth selectivity is on glucose, and selection for bacterial cells with the ability to grow on toluene is reduced. FIG. 2 illustrates a typical nitrogen-limited run at a dilution rate of 0.195 $hr^{-1}$. Under nitrogen-limited conditions, the stability of the mutant strain population is significantly improved (over 20 residence times vs. 2–3 residence times under carbon limited conditions).

Similar nutrient-limitation effects are observed when the above described type of bioconversion system is phosphorus-limited or iron-limited rather than nitrogen-limited. The nutrient-limitation effects are also operative for other mutant populations, such as a *Pseudomonas putida* Biotype A ATCC No. 39,119 type of mutant strain which is adapted to convert non-growth xylene carbon source to p-cresol.

What is claimed is:

1. A method of stabilizing a homogeneous population of a *Pseudomonas putida* Biotype a mutant microorganisms in a bioconversion system whereby growth of revertant cells is suppressed, which comprises cultivating the mutant under nitrogen limited conditions and maintaining the concentration of the nitrogen such that the growth rate is nitrogen controlled and results inthe enhanced stability of said mutant and the substantially retained ability of said mutant to convert a non-growth toluene carbon source by the ortho metabolic pathway to muconic acid, and wherein said *Pseudomonas putida* Biotype A microorganism is a mutant strain having the following characteristics:
    (a) Possesses catechol 1,2-oxygenase enzyme with activity that is not inhibited in the presence of a low level of muconic acid in a growth medium;
    (b) lacks active catechol 2,3-oxygenase enzyme;
    (c) lacks active muconate lactonizing enzyme; and
    (d) cells are rod shaped, vigorously motile and polarly flagellated.
2. A method in accordance with claim 1 wherein the bioconversion system is operating in steady state continuous mode.
3. A process in accordance with claim 1 wherein the *Pseudomonas putida* Biotype A mutant strain microorganism is ATCC No. 31,916.
4. A method in accordance with claim 1 wherein the non-growth toluene carbon source is converted to muconic acid at a rate of at least about 200 milligrams of muconic acid per dry weight gram of cells per hour, with an accumulation of greater than about one gram of muconic acid per liter of bioconversion medium.

* * * * *